United States Patent [19]

Chaoui

[11] Patent Number: 4,489,440
[45] Date of Patent: Dec. 18, 1984

[54] PRESSURE-COMPENSATED PNEUMATIC SPEECH SIMULATOR

[75] Inventor: Samir M. Chaoui, Brea, Calif.
[73] Assignee: Bear Medical Systems, Inc., Riverside, Calif.
[21] Appl. No.: 542,169
[22] Filed: Oct. 14, 1983
[51] Int. Cl.³ ............................................. A61F 1/20
[52] U.S. Cl. ............................................ 381/70; 3/1.3
[58] Field of Search ............................. 381/70; 3/1.3

[56] References Cited

U.S. PATENT DOCUMENTS

| | | | |
|---|---|---|---|
| 1,867,350 | 7/1932 | Burchett | 3/1.3 |
| 1,910,966 | 5/1933 | Riesz et al. | 3/1.3 |
| 4,292,472 | 9/1981 | Lennox | 179/1 AL |
| 4,338,488 | 7/1982 | Lennox | 179/1 AL |

Primary Examiner—Gene Z. Rubinson
Assistant Examiner—W. J. Brady
Attorney, Agent, or Firm—Howard J. Klein

[57] ABSTRACT

A pneumatic speech simulator has a vibratory tone-generating element which produces an audible tone in response to the flow of pressurized air within a predetermined pressure range, said tone being transmitted to a patient's pharyngeal region by a conduit, such as a nasal catheter. The simulator includes a pressure compensation valve, upstream from the tone-generating element, which maintains the pressure experienced by the tone-generating element within its operating range as the pneumatic resistance of tone-transmitting conduit is increased due to partial or total blockage.

20 Claims, 4 Drawing Figures

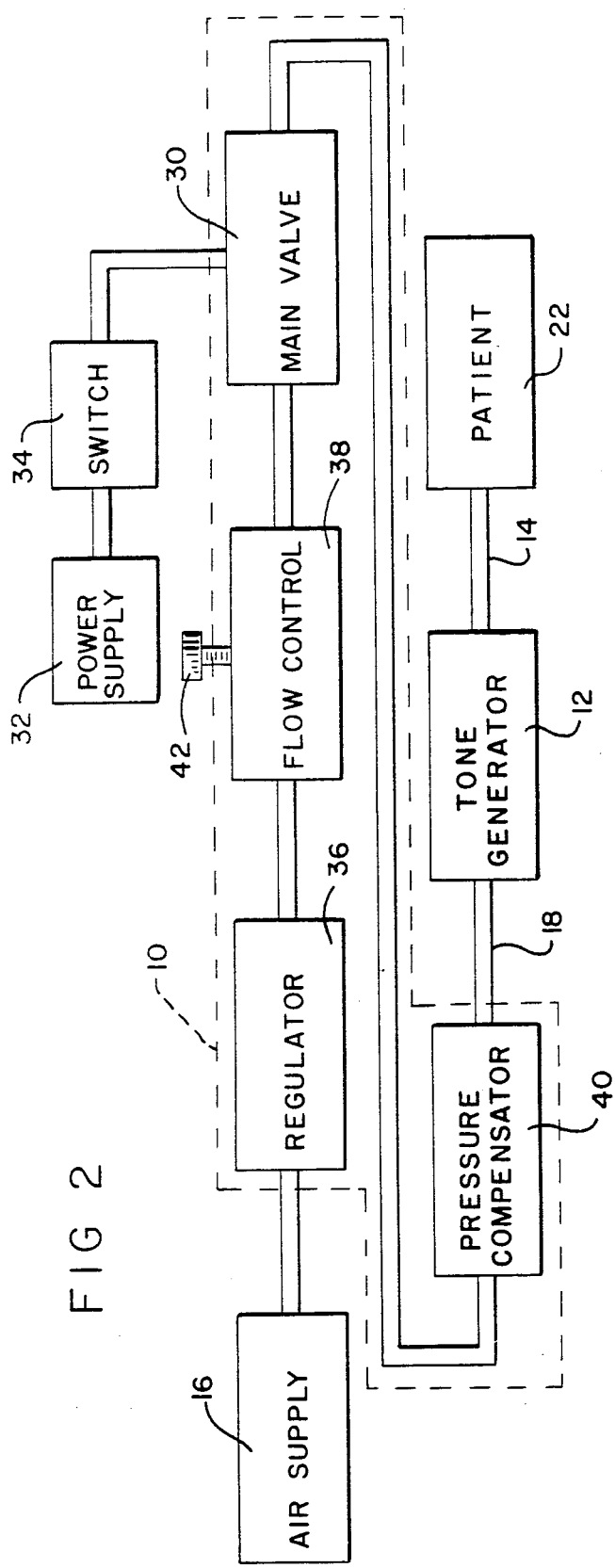
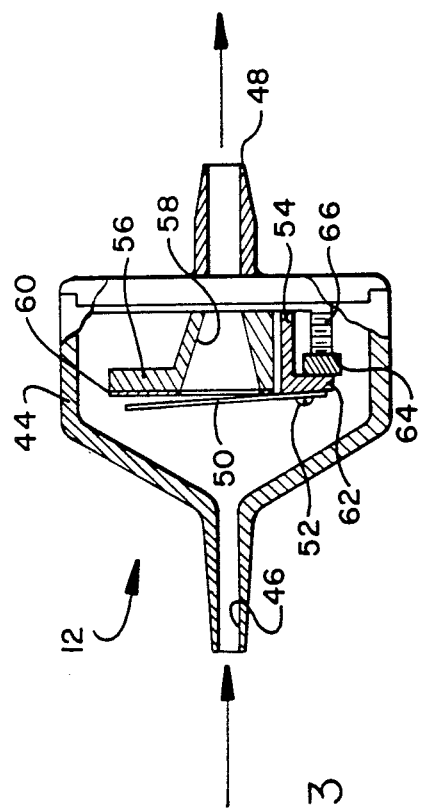
FIG 2
FIG 3

PRESSURE-COMPENSATED PNEUMATIC SPEECH SIMULATOR

BACKGROUND OF THE INVENTION

The present invention relates generally to the field of devices which provide the ability to speak for people whose larynxes have been removed or rendered inoperative. Specifically, the invention relates to the category of such devices in which pressurized air from an external source is used to actuate a vibratory member, thereby producing a tone which is transmitted to the proximity of the pharyngeal cavity for articulation.

A patient undergoing mechanical ventilation cannot speak due to the interruption of air flow to the larynx as a result of the patient being intubated or tracheotomized. In addition, a patient may be rendered unable to speak after having undergone a laryngectomy to remove a diseased or damaged larynx. In either case, the inability to speak can be most frustrating. This problem can result in severe emotional distress in the case of quadriplegic patients, who cannot write or gesture, and are thus left with no means whatsoever to communicate effectively.

Various types of artificial speech devices have been developed to address this problem. One type, which has shown promise recently, comprises a tone-generating mechanism (usually a vibratory reed), which is actuated by an external source of pressurized air. The reed, which is housed externally to the patient, produces a tone which is then transmitted, via a nasal catheter, to the pharyngeal region of the patient, so that speech sounds can be articulated by the mouth. The flow of air to the tone-generating mechanism is started and interrupted by a solenoid valve, which can be actuated by a hand switch, or by a switch operated by the wrinkling of the patient's brow, as disclosed in U.S. Pat. No. 4,338,488, for example.

While devices of this type have demonstrated satisfactory results, their operation is at times sensitive to conditions of obstructed air flow downstream from the tone generator. Obstructed, or partially obstructed, air flow can occur when mucous or saliva enters the patient end of the nasal catheter, or when the catheter becomes twisted or kinked. The result is an increase in air flow resistance, which translates as a buildup of pressure on the upstream side of the tone-generating reed. This increase in upstream pressure will, above a certain level, collapse the reed, making the device inoperative. If air from the pressurized source continues to flow without pressure relief, damage can occur to the device.

Therefore, some means has been sought to allow the tone-generating mechanism to operate even with a restricted air flow, and to provide overpressure relief in the event of a total or near total air flow blockage in the catheter.

SUMMARY OF THE INVENTION

Broadly, the present invention is a pneumatically operated speech simulator comprising a tone-generating element (e.g., a reed), actuated by pressurized air to produce a tone. The tone is transmitted, via a nasal catheter, to the pharyngeal region of the patient, near the uvula. The air flow to the tone-generating element is controlled by a solenoid valve, actuated by a switch operated by some part of the patient's body, which can be controllably moved by the patient. A pressure compensation valve is installed in the air flow line upstream of the tone-generating element. The pressure compensation valve serves to maintain the air pressure at the tone-generating element within predetermined operating limits even when the flow through the catheter is restricted. This valve also provides a pressure-relief function when total or near total blockage of the catheter occurs, thereby minimizing the probability of damage to the system.

The invention may also advantageously incorporate a flow-control valve to vary the air flow rate through the tone-generating element, thereby altering the volume of the generated tone. This valve is advantageously placed upstream from the solenoid-actuated main valve which, in turn, is placed upstream from the compensation valve.

In addition, a pressure regulating valve may be placed upstream from the flow-control valve to drop the pressure from the pressurized air source to a suitable operating pressure.

The pressure compensation valve, which forms a novel part of the invention, comprises a chamber having an inlet and an outlet which are in unobstructed fluid communication with each other. An exhaust port from the chamber is, at less than the normal operating pressures, blocked off by a spring-biased valving element. When the pressure experienced by the valving element is sufficient to overcome the spring bias, the exhaust port is opened, allowing air to flow to the ambient atmosphere. The spring bias is set so that the exhaust port is opened when the pressure reaches or exceeds the normal operating pressure, so that the outlet pressure is maintained at the normal operating pressure, or slightly above it. Thus, excess pressures which can collapse the tone-generating reed, or cause damage, are prevented.

As will be better appreciated from the detailed description which follows, the present invention effectively and reliably minimizes the aforementioned concerns arising from partial or total obstruction of the air flow through the catheter. This function is performed using a mechanism which is relatively simple and economical to construct and to adapt to a wide variety of clinical needs.

BRIEF DESCRIPTION OF THE DRAWINGS

FIG. 2 is a schematic representation of the pneumatic speech simulator of FIG. 1, showing the major components of the control unit;

FIG. 3 is an elevational view, partially in cross-section, of the tone generator used in the present invention.

DETAILED DESCRIPTION OF A PREFERRED EMBODIMENT

Figure 1:
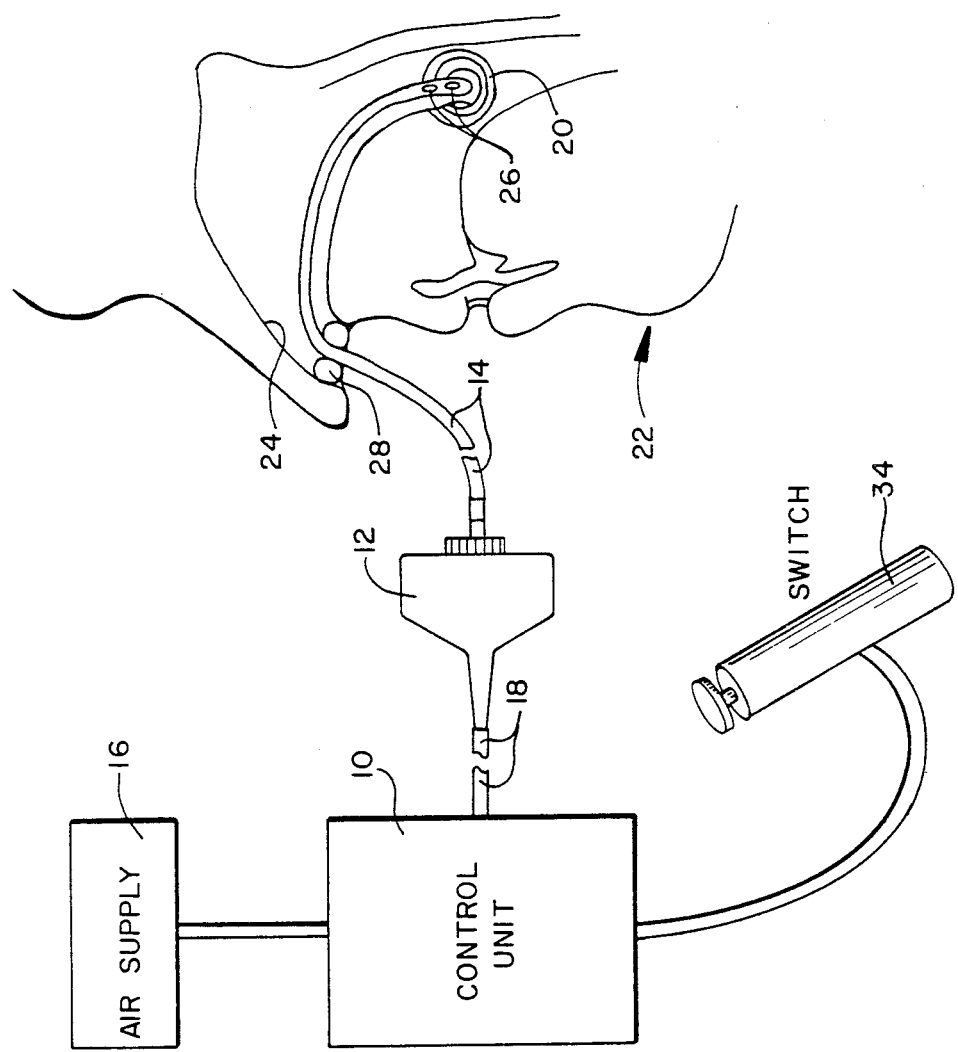
FIG. 1 is a semischematic view of a pneumatic speech simulator in accordance with the present invention.

Referring first to FIG. 1, a preferred embodiment of the present invention comprises a control unit 10, a tone-generating unit 12, and a nasal catheter 14. The control unit, as will be described in further detail below, receives air from a pressurized air supply 16, and then pneumatically treats the air for delivery to the tone-generating unit 12 via a flexible conduit 18. From the tone-generating unit, the air, carrying an audio-frequency tone, is conducted via the nasal catheter 14 into the pharyngeal region 20 of a patient 22 through the patient's nasal passages 24, as shown. The air is discharged into the pharynx 20 via fenestrations 26 in the proximity of the uvula (not shown). The air, introduced into this part of the pharynx, and vibrating with an audible tone, provides the patient with the means easily to articulate audible speech. The catheter 14 may advantageously be worn with a foam ring 28 inserted in the nostril for greater comfort.

The control unit 10 delivers pressurized air to the tone-generating unit 12 in response to the opening of a main valve 30 (FIG. 2) contained within the control unit. This main valve 30 is preferably of the solenoid-actuated type, well-known in the art. The solenoid is energized by a suitable power supply 32 (FIG. 2), which may either be contained within the control unit or be external to it. A low voltage (e.g., 9 volt) D.C. power supply is preferred, and this can take the form of a battery, or an A.C. to D.C. converter. Alternatively, power can be tapped from a suitable outlet frequently provided on medical ventilators. In any case, the energization of the solenoid valve 30 is controlled by a switch 34. As shown in FIG. 1, the switch 34 may be a conventional push-button switch. In the case of a patient who does not have use of his hands, such as a quadriplegic, a switch which is actuated by the wrinkling of the patient's brow can be used, as disclosed in U.S. Pat. No. 4,338,488. The particular configuration of the switch may be dictated by the physical condition of the patient; but, in any event, the switch 34 should be such as can be actuated by a controllable movement of some part of the patient's body.

Referring now to FIG. 2, the major components of the control unit 10 are shown in the context of a system flow diagram, said components being shown as enclosed within a dashed outline. In a preferred embodiment, the control unit 10 contains a pressure regulator 36, an adjustable flow control valve 38, the main (solenoid-actuated) valve 30, and a pressure compensation valve 40. The power supply 32, for the main valve 30, is typically external to the control unit; but, as previously mentioned, may be contained within it, if desired.

The air supply 16 may be a compressed air cylinder, or the compressed air supply typically found in a hospital room. Air from such sources is typically pressurized to a range of about 40 psi to about 90 psi. The regulator 36 receives the air from the supply 16 and regulates the static pressure down to about 30 psi.

Assuming the main valve 30 has been opened, air flows through the adjustable flow control valve 38, which may comprise a conventional needle valve, adjustable by means of a dial or knob 42. Using the flow control valve 38, the flow rate through the system may be adjusted from about 7.5 to about 10 liters per minute. As will be seen, the volume of the tone produced by the tone generator will be proportional to the flow rate of air through it.

From the main valve, the air flows through the pressure compensation valve 40 (to be described below), the tone generator 12, and into the patient 22 via the catheter 14.

The tone generator 12 is illustrated in FIG. 3. It comprises a housing 44, having an inlet 46 for receiving air from the compensation valve 40 (via the conduit 18), and an outlet 48 coupled to the catheter 14. The tone-generating element is a metal reed 50, which is mounted at one end (as by a screw 52) to a somewhat resilient support 54. The reed 50 may be a thin leaf of stainless steel, for example, with a thickness on the order of 5 mils. Adjacent to and spaced from the support 54 is a base or reed seat 56, having a passage 58 therethrough communicating with the outlet 48. A resilient pad 60, which softens the tone of the vibrating reed, is fixed to the upstream side of the reed seat 56 and has a hole registering with the passage 58. The support 54 has a shoulder 62, the underside of which is engaged by a button 64 on the end of a set screw 66. By adjustment of the set screw 66, the reed 50 can be tensioned via the support 54, and angled away from the reed seat 56, so that it vibrates with an audible tone (e.g., approximately 120 to 260 hertz) in response to the flow of air past it. The amplitude of the vibration, and therefore the volume of the tone produced, is proportional to the flow rate of the air. The vibrating air is conducted down the passage 58, through the outlet 48, and into the catheter 14. Typically, with flow rates in the aforementioned range, the reed 50 will suitably vibrate in response to dynamic air pressures in the range from about 70 or 80 $cmH_2O$ to about 100 or 110 $cmH_2O$. If, for some reason (as explained below), the dynamic pressure experienced by the reed 50 exceeds this range, it will collapse against the reed seat 56, and the device will be rendered inoperative.

Figure 4:
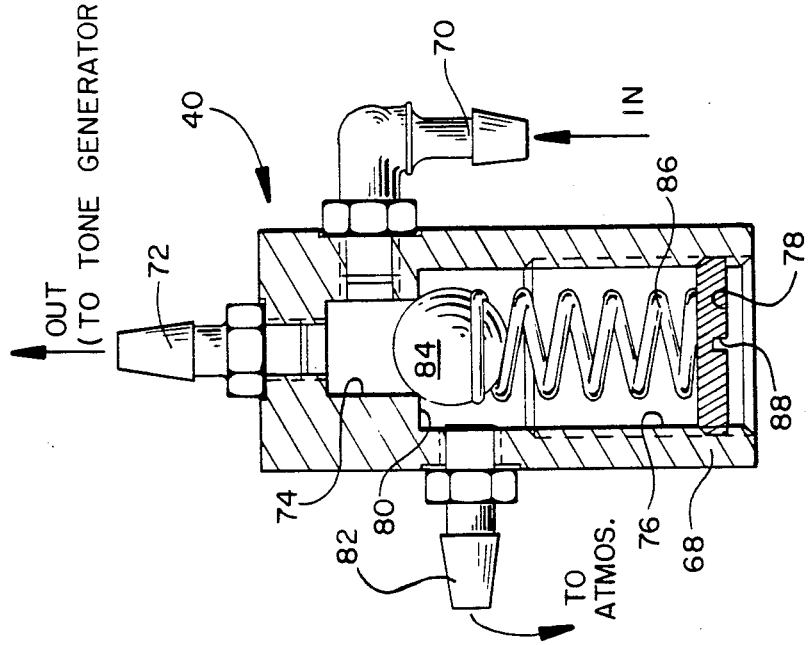
FIG. 4 is an elevational view, partially in cross-section, of the pressure compensation valve used in the present invention.

To mitigate against this effect, the present invention includes the pressure compensation valve 40, which is placed in the air flow path between the tone generator 12 and the main valve 30, as shown in FIG. 2. The compensation valve 40 itself is illustrated in FIG. 4. It comprises a housing 68 having an inlet 70 for receiving air from the main valve 30, and an outlet 72 for discharging air into the conduit 18 leading to the tone-generator inlet 46. One end of the housing 68 has a hollow bore 74 providing a free-flow passage from the inlet 70 to the outlet 72, which are preferably arranged at right angles to each other, as shown. The major part of the housing's interior comprises a chamber 76, having a distal end closed by an end cap 78 and a proximal end communicating with the bore 74. The juncture between the bore 74 and the chamber 76 is defined by an annular shoulder 80. A vent or exhaust port 82 leads from the chamber 76 to the atmosphere.

A valving element 84, preferably spherical, as shown, is biased against the shoulder 80 by a spring 86, thereby blocking the flow of air from the inlet 70 to the exhaust port 82. All air flow is thus from the inlet 70 to the outlet 72 through the bore 74, with little pneumatic resistance. When the pressure at the outlet 72 exceeds the biasing force of the spring 86, the valving element 84 is lifted off of the shoulder 80, opening a flow path from the inlet 70 to the exhaust port 82. In this manner, the valve 40 regulates the pressure at the outlet 72 to approximately the biasing force of the spring 86. This biasing force (and thus the regulated pressure) can be calibrated to a particular nominal pressure by varying the compression of the spring 86. To this end, it is advantageous to have the end cap 78 and the chamber wall threaded, so that the end cap can be moved to adjust the spring compression. A slot 88 in the end cap 78 facilitates its turning by a screwdriver or the like.

In the context of the present invention, the compensation valve works as follows: Should the catheter 14 become partially obstructed due to its being kinked or pinched, or from the clogging of the fenestrations 26 by mucous or saliva, the pneumatic resistance of the catheter 14 will increase. If the flow rate of air is maintained, an increased dynamic pressure will be experienced by the reed 50. The reed 50, as previously mentioned, will collapse and cease to vibrate when this pressure exceeds a certain point. This characteristic would make successful use of the speech simulator dependent upon constant vigilance to ensure a clear flow passage through the catheter.

The pressure compensation valve, however, minimizes the possibility of reed collapse. As previously discussed, when the outlet pressure of the compensation valve exceeds the bias force of the spring 86, the exhaust port flow path is at least partially opened, by movement of the valving element 84 off of the shoulder 80, allowing the bleeding or venting of air to the atmosphere through the exhaust port 82. The pressure at the outlet 72 of the compensation valve 40 is substantially the same as the pressure in the tone-generating unit 12. Therefore, if the valve 40 is calibrated to open the exhaust port flow path at a pressure that is within the operating pressure range of the reed 50 (preferably near the lower end of the range), excess pressure will be vented via the exhaust port, thereby maintaining the pressure experienced by the reed within its operating range.

The higher the pneumatic resistance of the catheter, the greater the instantaneous dynamic pressure will be at the compensation valve outlet, and the wider the valve will open (by further displacement of the valving element 84 from the flow path between the inlet 70 and the exhaust port 84), thereby bleeding off pressure faster to maintain the tone-generator within its operable pressure limits. If the catheter 14 becomes completely obstructed, the compensation valve 40 will act as an over-pressure relief valve, keeping the system pressure within tolerable limits, and thereby preventing possible damage to the components of the system.

Thus, it can be seen that the addition of the compensation valve allows the pneumatic speech simulator to be used without the need constantly to clear the catheter. Not only does this add to the comfort and convenience of use, but it avoids the need for frequent removal and re-insertion of the catheter, with resultant irritation of the delicate nasal passages. This result is achieved without adding undue complexity to the simulator, thereby providing for relative economy of manufacture and simplicity of maintenance.

While a preferred embodiment of the invention has been disclosed, it should be understood that several variations and modifications will suggest themselves to those skilled in the pertinent arts. For example, it has been mentioned above that the switch 34 can assume a number of configurations. Likewise, the tone-generating unit 12 may be modified in a number of ways (for example, in the configuration of the reed and in its manner of mounting) to suit varying clinical needs. Furthermore, the configuration of the compensation valve shown in the drawings, and described above, is exemplary only, and may be modified to suit particular applications. These and other modifications should be considered within the spirit and scope of the invention, as defined by the claims which follow.

What is claimed is:

1. A pneumatic speech simulator, of the type having means defining a flow path for conducting a flow of pressurized air from a source into the throat of a patient, tone-generating means in said flow path, said tone generating means being responsive to air pressures within a predetermined range to produce an audible tone, and means actuatable by said patient for controllably starting and stopping said flow of air, wherein the improvement comprises:

pressure responsive means in said flow path for maintaining the pressure experienced by said tone-generating means within said predetermined range as the pneumatic resistance of said flow path downstream from said tone-generating means increases.

2. The speech simulator of claim 1, wherein said pressure-responsive means is located upstream from said tone-generating means.

3. The speech simulator of claim 1, wherein said pressure-responsive means comprises valving means, responsive to the pressure in said flow path, for venting air from said flow path in response to pressures above the lower limit of said predetermined pressure range.

4. The speech simulator of claim 1, wherein the improvement further comprises:

means for varying the amplitude of the tone generated by said tone-generating means.

5. The speech simulator of claim 4, wherein said amplitude-varying means comprises:

flow-controlling means for controllably varying the flow-rate of the air impinging on said tone-generating means.

6. The speech simulator of claim 2, wherein said valving means comprises:

a housing having an inlet for receiving air from said source of pressurized air, an outlet fluidly coupled to said tone-generating means, and an exhaust port venting to atmosphere; first means in said housing defining a first flow path from said inlet to said outlet;

second means in said housing defining a second flow path from said inlet to said exhaust port;

a valving element normally blocking said second flow path; and biasing means acting on said valving element for allowing said valving element to be at least partially displaced from said second flow path in response to pressures at said outlet above the lower limit of said predetermined pressure range.

7. The speech simulator of claim 1, wherein said flow path-defining means comprises:

a first conduit for conducting air from said pressure-responsive means to said tone-generating means; and a second conduit for conducting air from said tone-generating means to the pharyngeal region of said patient's throat.

8. The speech simulator of claim 7, wherein said tone-generating means comprises:

a housing having an inlet fluidly coupled to said first conduit and an outlet fluidly coupled to said second conduit; and a vibratory reed element mounted in said housing between said inlet and said outlet for vibration with said audible tone in response to the flow of air from said inlet to said outlet.

9. The speech simulator of claim 8, wherein said tone-generating means further comprises:

a reed seat in said housing having a passage therethrough in communication with said outlet;

a reed support attached to one end of said reed and supporting said reed in spaced relationship to the upstream end of said reed seat; and means engaging said reed support for tensioning said reed and angling said reed with respect to said reed seat so that said reed vibrates with said audible tone in response to said flow of air.

10. The speech simulator of claim 7, wherein said second conduit comprises a flexible nasal catheter having a first end coupled to said tone-generating means, a second end adapted to be inserted through said patient's nasal passages into the pharyngeal region of said patient near the uvula of said patient, said second end having a fenestration to allow air to flow into said pharyngeal region.

11. A pneumatic speech simulator, of the type having means defining a flow path for conducting a flow of pressurized air from a source into the pharynx of a patient, vibratory tone-generating means in said flow path adapted to produce an audible tone in response to air pressures within a predetermined range, and means actuatable by said patient for controllably starting and stopping the flow of air through said tone-generating means, wherein said flow path defining means includes a flexible nasal catheter having a fenestrated end adapted for positioning in said pharynx, and wherein the improvement comprises:
pressure-responsive means in said flow path, upstream from said tone-generating means, for venting air from said flow path in response to dynamic pressures in said flow path above a pre-selected pressure at or slightly above the lower limit of said predetermined pressure range, thereby maintaining the pressure experienced by said tone-generating means within said predetermined range as the pneumatic resistance of said catheter increases.

12. The speech simulator of claim 11, wherein the improvement further comprises:
flow-controlling means for controllably varying the flow rate of air through said tone-generating means and thereby varying the amplitude of the generating audible tone.

13. The speech simulator of claim 11, wherein said pressure-responsive means comprises:
a housing having an inlet for receiving air from said source, an outlet fluidly coupled to said tone-generating means, and an exhaust port venting to atmosphere;
a first flow path in said housing from said inlet to said outlet;
a second flow path in said housing from said inlet to said exhaust port; and
valving means in said housing for closing said second flow path when the pressure at said outlet is below said preselected pressure and opening, said second flow path when the pressure at said outlet is approximately at said preselected pressure.

14. The speech simulator of claim 13, wherein said valving means comprises:
a valving element normally blocking said second flow path; and
biasing means, acting on said valving element, for allowing said valving element to be at least partially displaced from said second flow path in response to pressures at said outlet approximately equal to said preselected pressure.

15. The speech simulator of claim 14, wherein said valving element is displaced from said second flow path by an amount approximately proportional to the pressure at said outlet within said predetermined pressure range.

16. The speech simulator of claim 13, further comprising:
calibration means, operative on said valving means, for controllably varying said preselected pressure.

17. A speech simulator, operable on pressurized air, comprising:
regulator means for regulating the static pressure of air from a pressurized source;
vibratory tone-generating means, fluidly coupled to said regulator means, for generating an audile tone in response to a flow of air therethrough and operable within a predetermined range of dynamic pressures;
a flexible nasal catheter having a first end fluidly coupled to said tone-generating means and a second end adapted for insertion through the nasal passages of a patient to be positioned in the pharynx of said patient, said catheter having a fenestration proximate said second end;
main valving means, actuatable by said patient, for controllably starting and stopping the flow of air through said tone-generating means; and
pressure-compensating means, upstream from said tone-generating means and downstream from said regulator means, for venting air received from said regulator means in response to dynamic pressures at said tone-generating means above a pre-selected pressure at or slightly above the lower limit of said predetermined pressure range, thereby maintaining the pressure experienced by said tone-generating means within said predetermined range as the pneumatic resistance of said catheter increases.

18. The speech simulator of claim 17, wherein said pressure-compensating means comprises:
a housing having an inlet fluidly coupled to said regulator, an outlet fluidly coupled to said tone-generating means, and an exhaust port venting to atmosphere;
a first flow path in said housing from said inlet to said outlet;
a second flow path in said housing from said inlet to said exhaust port; and valving means in said housing for closing said second flow path when the pressure at said outlet is below said preselected pressure and opening said second flow path when the pressure at said outlet is approximately at said preselected pressure.

19. The speech simulator of claim 18, wherein said valving means comprises:
a valving element normally blocking said second flow
path; and
biasing means, acting on said valving element, for allowing said valving element to be at least partially displaced from said second flow path in response to pressures at said outlet approximately equal to said preselected pressure.

20. The speech simulator of claim 17, wherein the amplitude of the tone produced by said tone-generating means is substantially proportional to the flow rate through said tone-generating means, and wherein said speech simulator further comprises:
means between said regulator and said tone-generating means for controllably varying the flow rate of air through said tone-generating means.

* * * * *